United States Patent
Wen

(10) Patent No.: US 8,026,916 B2
(45) Date of Patent: Sep. 27, 2011

(54) IMAGE-BASED VIEWING SYSTEM

(75) Inventor: Huafeng Wen, Redwood City, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 12/168,718

(22) Filed: Jul. 7, 2008

(65) Prior Publication Data

US 2008/0316209 A1 Dec. 25, 2008

Related U.S. Application Data

(63) Continuation of application No. 11/542,682, filed on Oct. 2, 2006, now abandoned, which is a continuation of application No. 11/013,146, filed on Dec. 14, 2004, now abandoned.

(51) Int. Cl.
*G06T 15/30* (2011.01)

(52) U.S. Cl. ............... 345/423; 345/419; 345/420

(58) Field of Classification Search .............. None
See application file for complete search history.

(56) References Cited

U.S. PATENT DOCUMENTS

| | | | |
|---|---|---|---|
| 7,065,243 B2 * | 6/2006 | Boland et al. | 382/154 |
| 7,134,874 B2 * | 11/2006 | Chishti et al. | 433/24 |
| 7,228,191 B2 * | 6/2007 | Hofmeister et al. | 700/98 |
| 7,234,937 B2 * | 6/2007 | Sachdeva et al. | 433/24 |
| 7,660,623 B2 * | 2/2010 | Hunter et al. | 600/424 |
| 7,716,024 B2 * | 5/2010 | Hultgren et al. | 703/6 |
| 2002/0077540 A1 * | 6/2002 | Kienzle, III | 600/424 |
| 2002/0085046 A1 * | 7/2002 | Furuta et al. | 345/848 |
| 2003/0001834 A1 * | 1/2003 | Chaw et al. | 345/418 |
| 2003/0065278 A1 * | 4/2003 | Rubinstenn et al. | 600/587 |
| 2003/0123713 A1 * | 7/2003 | Geng | 382/118 |
| 2004/0068172 A1 * | 4/2004 | Nowinski et al. | 600/407 |
| 2004/0175039 A1 * | 9/2004 | Miller | 382/181 |
| 2004/0197727 A1 * | 10/2004 | Sachdeva et al. | 433/24 |
| 2005/0033142 A1 * | 2/2005 | Madden et al. | 600/407 |

OTHER PUBLICATIONS

Beier, T., Neely, S., Feature-based image metamorphosis, Jul. 1992, ACM SIGGRAPH Computer Graphics, vol. 26, Issue 2, pp. 35-42.*
Gregory, A., State, A., Lin, M., Manocha, D., Livingston, M., Feature-based Surface Decomposition for Correspondence and Morphing between Polyhedra, Jun. 1998, Proceedings of the Computer Animation 1998, pp. 64-75.*

* cited by examiner

*Primary Examiner* — Said Broome
(74) *Attorney, Agent, or Firm* — Brooks, Cameron & Huebsch, PLLC

(57) ABSTRACT

Systems and methods are disclosed for visualizing changes in a three dimensional (3D) model by receiving an initial 3D model; determining a target 3D model; and generating one or more intermediate 3D models by morphing one or more of the 3D models.

25 Claims, 5 Drawing Sheets

IMAGE-BASED VIEWING SYSTEM

CROSS-REFERENCE TO RELATED APPLICATIONS

This application is a continuation of U.S. patent application Ser. No. 11/542,682, filed Oct. 2, 2006, entitled IMAGE-BASED ORTHODONTIC TREATMENT VIEWING SYSTEM, which is a continuation of U.S. patent application Ser. No. 11/013,146, filed Dec. 14, 2004, entitled IMAGE-BASED ORTHODONTIC TREATMENT VIEWING SYSTEM, both of which applications are incorporated herewith in their entirety.

FIELD OF INVENTION

The present invention relates to techniques for generating three dimensional (3D) graphics for various treatments.

BACKGROUND

Conventionally, a 3D modeling and rendering process is used for representing different views of a 3D scene. The usual steps in constructing a 3D model include: loading an image or previous saved work; displaying the image; identifying one or more object features in the image; finding the object features in 3D space; displaying a model of object features in 3D space; measuring lengths, distances and angles of the objects; and saving the work. These steps can be repeated until satisfactory results are obtained. This process requires a great deal of user interaction and is time-consuming. The user has to construct detailed models (e.g., polygon or wire frame) of the objects appearing in an image.

Once 3D models are obtained, the models may be animated by varying them and displaying the varied models at a predetermined frame rate. However, it is difficult to manipulate computer graphics representations of three-dimensional models, for example to rotate the object or "fly through" a scene. If many objects need to be displayed, or many surface textures need to be filled, the time required to compute new views can be prohibitive. The conventional 3D rendering process is thus compute intensive and also the rendering time depends on the complexity of the visible part of the scene.

On another note, in many graphics applications, a special effect operation known as "warping" or "morphing" is used to gradually transform one image into another image. This is accomplished by creating a smooth transitional link between the two images. Some computer programs, for example, use warping to generate an animation sequence using the image transformations. Such an animation might, for example, show a first person's face transforming into a second person's face.

The warping process preserves features associated with each image by mapping the features from a source image to corresponding features in a destination image. In particular, mesh warping warps a first image into a second image using a point-to-point mapping from the first image to the second image. A first lattice (mesh) is superimposed on the first image and second lattice is superimposed on the second image. For each point in the first lattice, a one-to-one correspondence with a corresponding point in the second lattice is defined. Mesh warping is generally described in George Wolberg, Digital Image Warping, IEEE Computer Society Press (1990). Variations on mesh warping include a version in which the user specifies lines on the first image corresponding to lines on the second image.

Morphing is a name for animation sequences which display gradual transformation. This concept has been used for transformations of 2D images, 3D polygons, and voxels. The morphing operation changes one picture to another by creating a smooth transitional link between the two pictures. The process preserves features associated with each image by mapping the features from a source image to corresponding features in a destination image. Morphing couples image warping with color interpolation. Image warping applies two dimensional geometric transformations on images to align their features geometrically, while color interpolation blends their colors. In this way, a seamless transition from one picture to another is achieved.

U.S. Pat. No. 6,268,846 discloses a computer-implemented method that generates a new view of a three-dimensional scene by receiving three or more pictures representing three or more different view points on a plane, each picture taken from a viewing direction perpendicular to the plane; selecting a new point on the plane; and generating the new view of the three dimensional scene from the new point by morphing among the three or more pictures.

U.S. Pat. No. 6,573,889 discloses a computer-implemented system that performs a conformal warp operation using a unique warping function to map a first area to a second area. The first area is defined by a first enclosing contour and the second area is defined by a second enclosing contour. The system defines the first enclosing contour; modifies the first enclosing contour into the second enclosing contour; generates an analytic function to conformally warp the first area into the second area; and performs the conformal warp using the analytic function. The system does not require the user to define mappings from individual points within the first contour to individual points within the second contour. Rather, the user needs to only specify the first and second contours and correspondences between them. This increases the ease of use with which the user can define a mapping between the first and second images and also allows for a more uniform warping which preserves angles.

SUMMARY

Systems and methods are disclosed for visualizing changes in a three dimensional (3D) model by receiving an initial 3D model for the patient; determining a target 3D model; and generating one or more intermediate 3D models by morphing one or more of the 3D models.

In one embodiment, 3D geometry information is used to morph an untreated photograph of a patient into a photo realistic rendering of post-treatment view(s) of a patient's teeth, face or organ based and predicted 3D geometry after treatment.

Advantages of the system include one or more of the following. The system enables patients/doctors/dentists to be able to look at photorealistic rendering of the patient as they would appear to be after treatment. In case of orthodontics for example, a patient will be able to see what kind of smile he or she would have after treatment. The system uses 3D morphing, which is an improvement over 2D morphing since true 3D models are generated for all intermediate models. The resulting 3D intermediate object can be processed with an environmental model such as lighting, color, texture etc to realistically render the intermediate stage. Camera viewpoints can be changed and the 3D models can render the intermediate object from any angle. The system permits the user to generate any desired 3D view, if provided with a small number of appropriately chosen starting images. The system avoids the need for 3D shape modeling. System performance is enhanced because the morphing process requires less memory space, disk space and processing power than the 3D shape modeling process. The resulting 3D images are lifelike and visually convincing because they are derived from images and not from geometric models. The system thus provides a powerful and lasting impression, engages audiences and creates a sense of reality and credibility.

DESCRIPTION OF THE DRAWINGS

Figure 1:
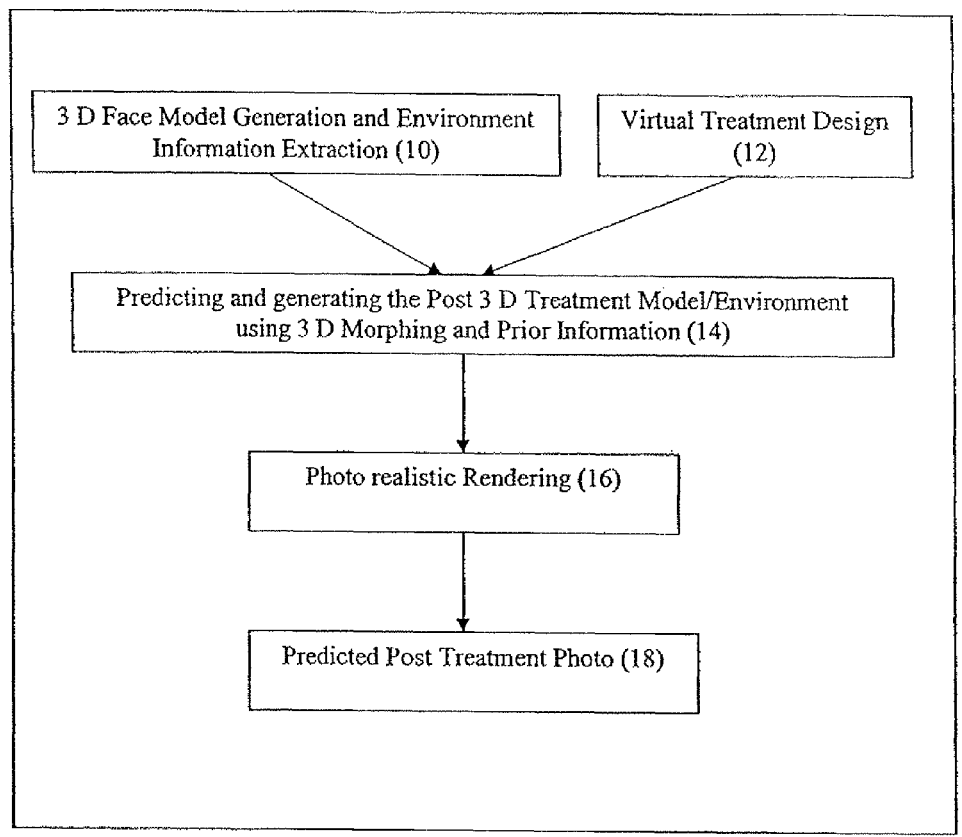
FIG. 1 shows an exemplary visualization process for 3D animation using morphing.

FIG. 1 shows an exemplary process that uses 3D geometry information to morph an untreated photograph of a patient into a photo realistic rendering of post-treatment view(s) of a patient's teeth, face or organ based and predicted 3D geometry after treatment.

The process of FIG. 1 first receives a 3D face model for the patient and extracts environment information from the model (10). Next, a Virtual Treatment is designed (12). The process then predicts and generates a Post-Treatment 3D Model/Environment using 3D Morphing and previously generated Information (14). A photo realistic image is then rendered (16), and the predicted Post-Treatment Photo can be viewed (18).

In the virtual treatment design (12), the system generates or otherwise obtains one or more treatment plans specifying the treatment process in which the teeth are moved in order to perform the orthodontic treatment. The input to this process is the 3D geometry of the patient's jaw and/or teeth. In this process, a computer or computer operators design treatments for the patient. This treatment results in a predicted shape/position for the jaw and teeth in it after the orthodontic treatment has been applied.

In the predicting and generating the 3D Post-Treatment Model/Environment (14), the Treatment Design is combined with the 3D Teeth/Face Model with texture, environment, shadow, shading information in order to predict the 3D Post Treatment Teeth/Jaw and/or face model which will include the changes in the 3D Geometry Position Texture Environment Shading and Shadow of the face.

Certain treatment design information such as how the teeth move during the orthodontic treatment and changes in the tooth movement can be used with the database on faces and teeth to determine how changes in a particular tooth position results in changes in the jaw and facial model. Since all data at this stage is 3D data, the system can compute the impact of any tooth movement using true 3D morphing of the facial model based on the prior knowledge of teeth and facial bone and tissue. In this manner, movements in the jaw/teeth result in changes to the 3D model of the teeth and face. Techniques such as collision computation between the jaw and the facial bone and tissue are used to calculate deformations on the face. The information is then combined with curves and surfaces based smoothing algorithms specialized for the 3D models and the database containing prior knowledge of faces to simulate the changes to the overall face due to localized changes in tooth position. The gradual changes in the teeth/face are visualized and computed using true 3D morphing.

At this stage, the 3D models and environmental information for the predicted post-treatment of facial and dental models are completed and the computed data can be sent to a photo realistic renderer for high quality rendering of the post-treatment teeth and/or face (16). The predicted post-treatment photo is then generated from the renderer (18).

Figure 2:
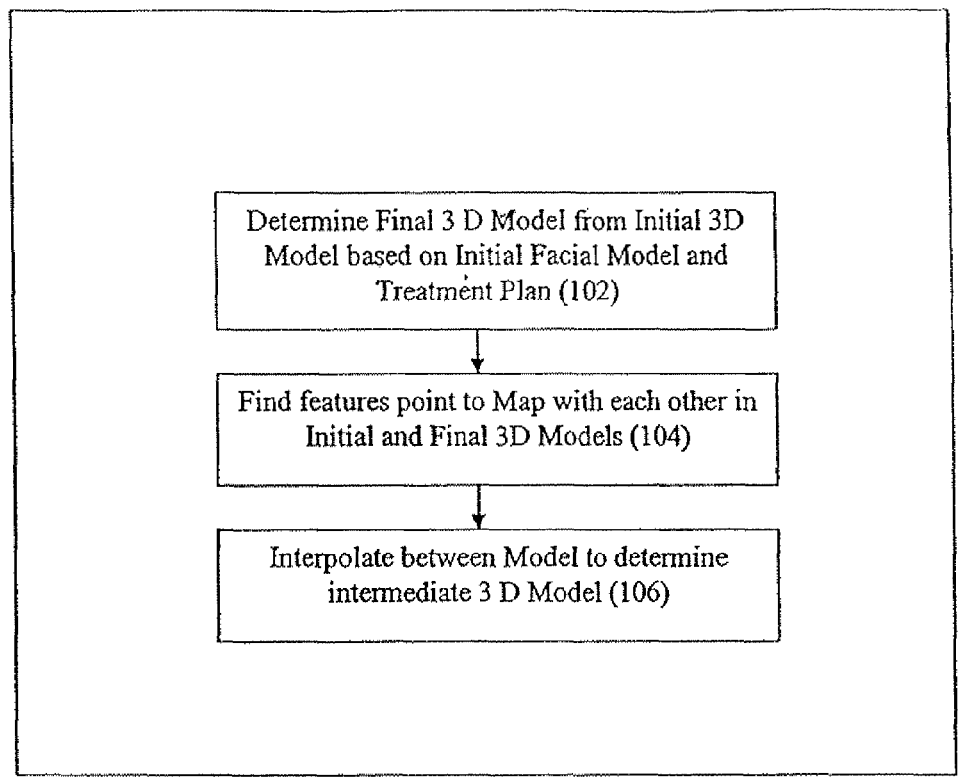
FIG. 2 shows an exemplary process for 3D morphing in the 3D visualization process of FIG. 1.

FIG. 2 shows an exemplary process for 3D morphing. The process determines a final 3D model from an initial 3D model based on an Initial Facial Model and Treatment Plan (102). Next, the process finds feature points to map corresponding features on the Initial and Final 3D models (104). Based on the mapping, the process interpolates between the initial and final models to determine intermediate 3D models (106). The result is a photo realistic rendering of the patient's jaw/teeth/face after the proposed treatment has been applied.

The morphing operation gradually converts one graphical object into another graphical object. Morphing is used to affect both the shape and also the attributes of graphical objects. 3D morphing is the process in which there is gradual transformation between 3D objects. Using start and final 3D models, a 3D morphing sequence is produced by interpolating these objects. For example, 3D objects are commonly represented using polyhedrons, i.e. vertices, edges, and faces. For these polyhedrons, the process results in a polyhedron sequence in which each intermediate polyhedron looks more like the final polyhedron and less like the start or beginning polyhedron.

In one implementation, the process morphs between objects described by a voxel representation. Morphing can include changes in the 3D model including possibly deformations, changes in the 3D structure, surface properties, among others. The process can morph surface features such as change the color attributes gradually. The color morphing can be used in gradually showing the whitening of teeth, for example.

The feature mapping may include teeth or lips on the initial and final models. Also, when using 3D polyhedral representation, the process specifies faces, edges, or vertices in each group. Alternatively, when using a voxel representation, appropriate voxels in each group are specified. The group concept can also be applied to the morphing of surface properties such as the case as in teeth whitening.

In one implementation, pseudo-code for the 3D Morphing algorithm is follows:

1. Determine final 3D Model using facial/teeth model based on the initial 3D model and the treatment plan and generate a final 3D model based on the treatment plan.

2. Map features from initial 3D Model to the final 3D model.

3. Interpolate the 3D models at any step to determine the intermediate 3D model (true 3D Model).

4. Apply true 3D model for realistic rendering.

Turning now to the generation of the patient 3D model (10), scanned information from various sources are combined to generate 3D model(s) for the face and jaw and teeth of the patient before treatment (initial model). The process also obtains the information about the rendering environment (e.g. shadows and shading and color information). The resulting detailed initial 3D model and rendering environment are stored for subsequent operations such as rendering/visualization as well as collision determination, among others. The process also receives information about the Treatment Design specifying each tooth movement during the orthodontic treatment. The information on the changes in the tooth movement are used in conjunction with. information on the faces and teeth to determine how a change in the tooth position changes the overall view of the teeth in the jaw and in the soft tissue of the face and the rest of the facial model. This is done using a true 3D model morphing. The 3D data is used to compute the impact of any tooth movement using true 3D morphing of the teeth/facial model based on previously determined teeth and facial model.

Patient data can be generated through a color 3D scan of the patient's face and can include other data such as X-Ray data and Cr data, among others. Alternatively, a picture of the patient can be used with a generic face model and the operation 10 can texture map the picture onto the 3D face. The original 2D pictures are saved in the process to eventually provide surface texture, shadow and shading information for the patient. The following exemplary data, among others, can be collected:

3D scan image of the patient's head/face. This is the how the patient currently looks before treatment such as data which represents the soft tissue of the face.

Untreated photo of the patient. 2D pictures are provided as input to texture mapping techniques and known facial models to generate a facial model based on 2D pictures as an alternative to a 3D scan.

3D scans for of the jaw and teeth of the patient to provide information on the initial orientation of the jaw and teeth prior to the treatment. X-Rays for Bone and tissue information.

Environmental information. This is used to obtain separate the color pigment information from the shading and shadow information of the patient.

The patient's color pigments can be separated from shadow/shading in photo of the patient. The system generates initial environmental information by placing light sources at known coordinates and using these coordinates as inputs to the system. Alternatively, lighting from many angles can be used so that there are no shadows and the system can subsequently incorporate lighting into the 3D environment.

In one implementation, the above data is combined to create a complete 3D model of the patient's face using the Patient's 3D Geometry, Texture, Environment Shading and Shadow. The result is a true Hierarchy model with bone, teeth, gingival, joint information, muscles, soft tissue, skin. Missing data such as internal muscle can be added using a data base of known facial models.

The result is the initial 3D orthodontic and facial model with environmental information extracted. This gives the system the ability to change direction of the light sources and see changes in shading and the shadows. The arrangement also provides thes the ability to extract the color of the patient skin.

In one implementation of the generation of 3D Face Model for the patient and extraction of environment, a true hierarchical face model with teeth, bone, joints, gingiva, muscle, soft tissue and skin. Changes in position/shape of one level of the hierarchy changes all dependent levels in the hierarchy. As an example a modification in the jaw bone will impact the muscle, soft tissue and skin. This includes changes in the gingiva.

The process extrapolates missing data using prior knowledge on the particular organ. For example, for missing data on a particular tooth, the system consults a database to estimate expected data for the tooth. For missing facial data, the system can check with a soft tissue database to estimate the muscle and internal tissue which are extrapolated.

The system also estimate the behavior of the organ based on its geometry and other model of the organ. An expert system computes the model of face and how the face should change if pressure is applied by moved teeth. In this manner, the impact of teeth movement on the face is determined. Changes in the gingival can also be determined using this model.

In one implementation, geometry subdivision and tessellation are used. Based on changes in the face caused by changes in teeth position, at times it is required to subdivide the soft face tissue geometry for a more detailed/smooth rendering. At other times the level of detail needs to be reduced. The model uses prior information to achieve this. True 3D morphing connects the initial and modified geometry for showing gradual changes in the face model.

In certain applications that need the external 3D model for the face and the 3D model for the jaw/teeth as well as internal model such as. The inner side of the facial tissue, and muscle tissue, hole filling and hidden geometry prediction operations are performed on the organ. The internal information is required in these applications to model the impact of changes at various level of model hierarchy on the overall model.

As an example, teeth movement can impact facial soft tissue or bone movements. Hence, jaw movements can impact the muscles and the face. A database containing prior knowledge can be used for generating the internal model information.

In one implementation, gingiva prediction is done. The model recomputes the gingivas geometry based on changes in other parts of the facial model to determine how teeth movement impacts the gingiva.

In another implementation, a texture based 3D geometry reconstruction is done. The actual face color/pigment is stored as a texture. Since different parts of the facial skin can have different colorations, texture maps store colors corresponding to each position on the face 3D model.

In another implementation, multiple cameras are used for photo geometry reconstruction. Multiple camera shots are used to generate the face geometry to produce a true 3D model of the face.

An alternate to scanning the model is to have a 2D picture of patient. The process then maps point(s) on the 2D picture to a 3D model using prior information on typical sets of heads 3D (for example by applying texture mapping). The simulated 3D head is used for making the final facial model.

Figure 3:
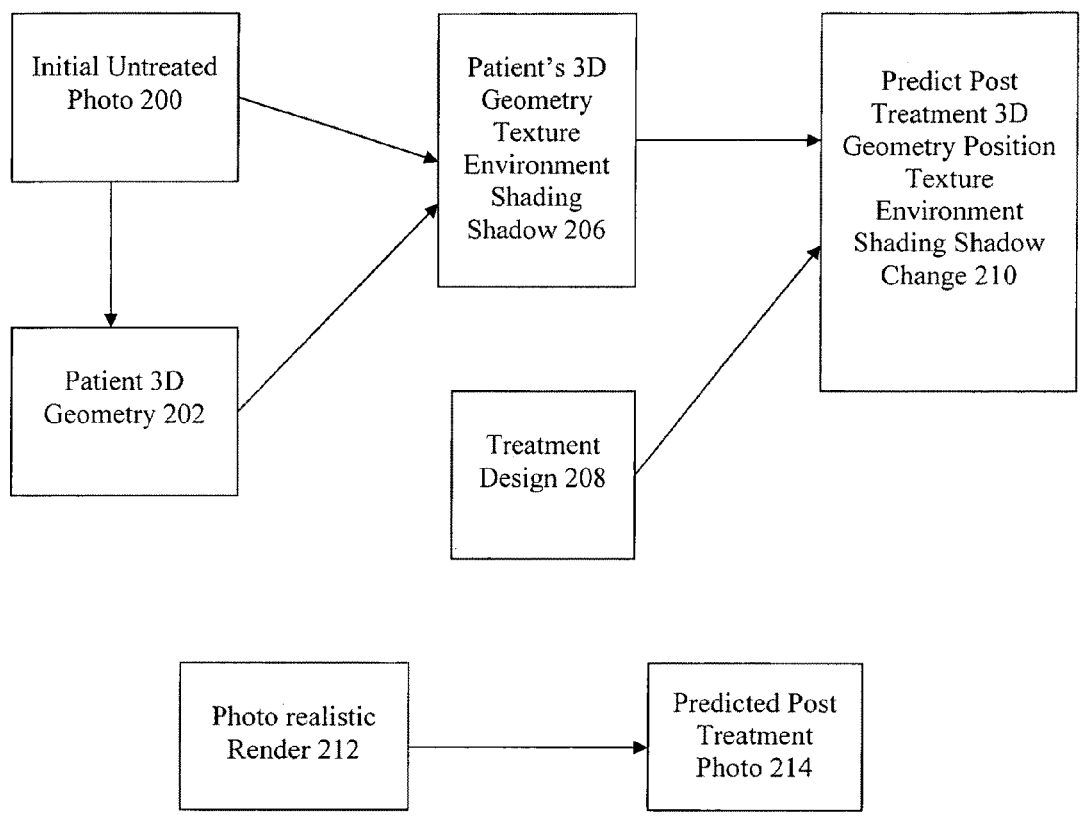
FIG. 3 shows a system for visualizing 3D animation.

FIG. 3 shows another implementation of a 3D morphing system for treatment planning purposes. Initial untreated photograph of a patient are scanned (200). From the scan, patient 3D geometry is determined (202). Next, exemplary 3D data is determined, for example, the Patient's 3D Geometry Texture, Environment, Shading, and Shadow (206). The output of 206 is combined with a treatment design or prescription (208) to arrive at a predicted Post Treatment 3D model with geometry, position, texture, environment, shading, and shadow, among others (210). The output is then rendered as a photo realistic output (212). The result can be used as predicted post-treatment photo (214).

Figure 4:
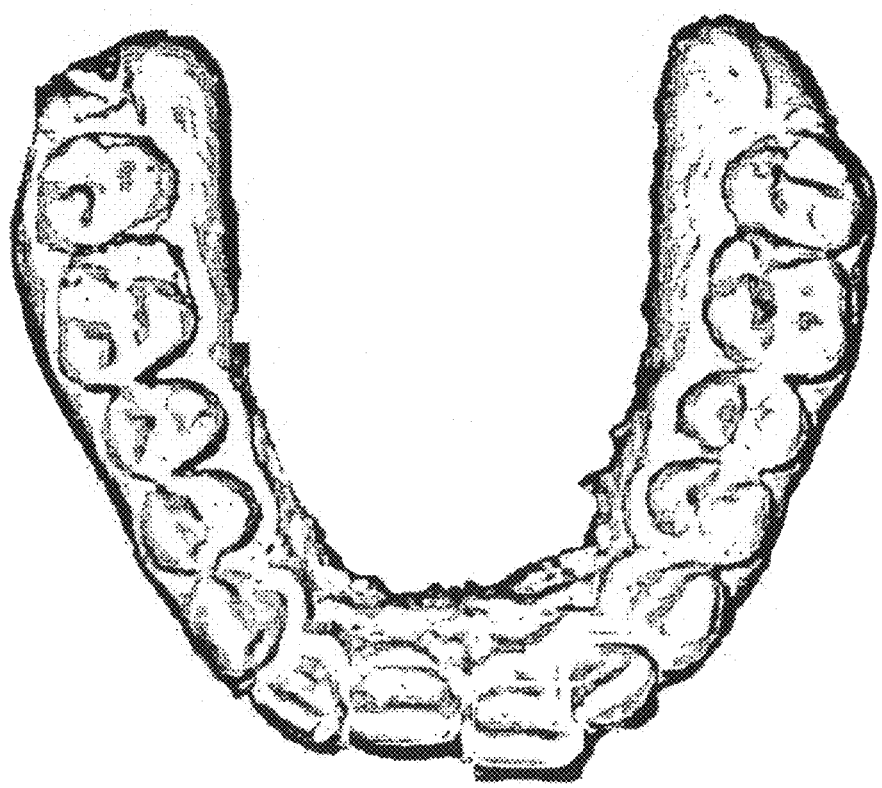
FIG. 4 shows exemplary teeth before morphing.
Figure 5:
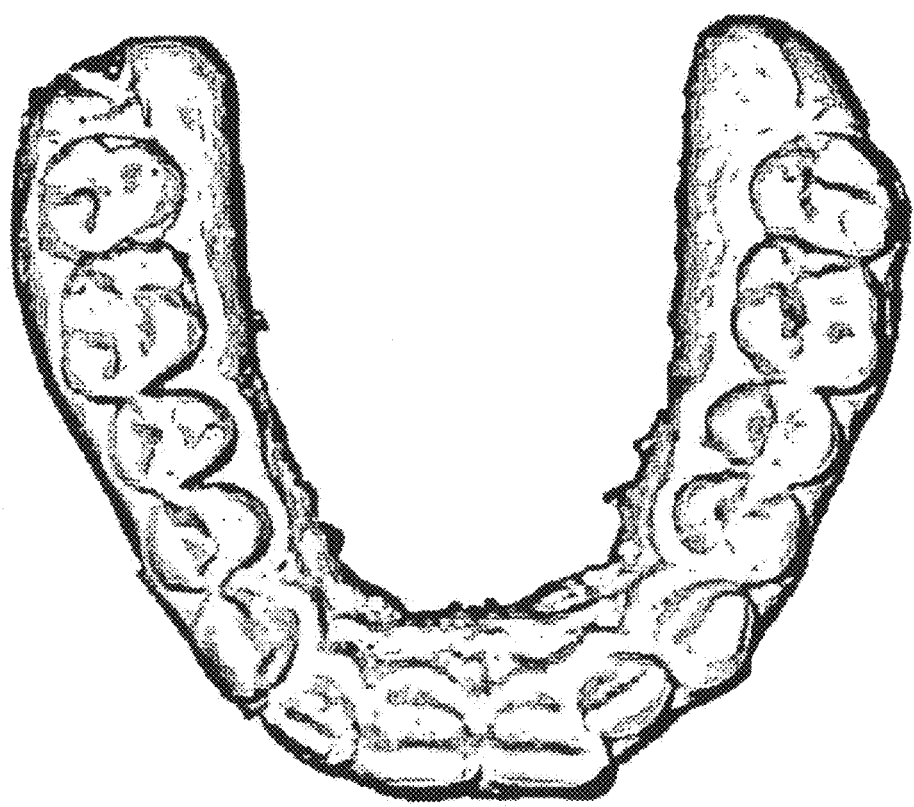
FIG. 5 shows an exemplary display of teeth after the 3D morphing process.

FIG. 4 shows exemplary teeth before morphing, while FIG. 5 shows an exemplary display of teeth after the 3D morphing process. The system enables patients, doctors, dentists and other interested parties to view photorealistic rendering of expected appearances of patients after treatment. In case of orthodontics for example, a patient can view his or her expected smile post-treatment.

The system can also be used for other medical, surgical simulation systems. Thus, for plastic surgery applications, the system can show the before and after results of the procedure. In tooth whitening applications, given an initial tooth color and given a target tooth color, the tooth surface color can be morphed to show changes in the tooth color and the impact on the patient face. The system can also be used to perform lip sync. The system can also perform face detection: depending of facial expression, a person can have multiple expressions on their face at different times and the model can simulate multiple expressions based on prior information and the multiple expressions can be compared to a scanned face for face detection. The system can also be applied to show wound healing on the face through progressive morphing. Additionally, a growth model based on a database of prior organ growth information to predict how an organ would be expected to grow and the growth can be visualized using morphing. For example, a hair growth model can show a person his or her expected appearance three to six months from the day of the haircut using one or more hair models.

The techniques described here may be implemented in hardware or software, or a combination of the two. Preferably, the techniques are implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

One such computer system includes a CPU, a RAM, a ROM and an I/O controller coupled by a CPU bus. The I/O controller is also coupled by an I/O bus to input devices such as a keyboard and a mouse, and output devices such as a monitor. The I/O controller also drives an I/O interface which in turn controls a removable disk drive such as a floppy disk, among others.

Variations are within the scope of the following claims. For example, instead of using a mouse as the input devices to the computer system, a pressure-sensitive pen or tablet may be used to generate the cursor position information. Moreover, each program is preferably implemented in a high level procedural or object-oriented programming language to communicate with a computer system. However, the programs can be implemented in assembly or machine language, if desired. In any case, the language may be a compiled or interpreted language.

Each such computer program is preferably stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

While the invention has been shown and described with reference to an embodiment thereof, those skilled in the art will understand that the above and other changes in form and detail may be made without departing from the spirit and scope of the following claims.

The invention claimed is:

1. A method for visualizing changes in a three dimensional (3D) model, comprising:
 generating initial environmental information by placing light sources at known coordinates when an initial 2D photograph of a person's hair is taken;
 receiving the initial 2D photograph of the person's hair;
 receiving an initial 3D model of the person's hair;
 designing a virtual hair growth, for the person's hair based at least partially on the initial 2D photograph, the initial 3D model, and a growth model using a database of prior hair growth information;
 determining a target 3D model of the hair for the person based on the initial 3D model and the virtual hair growth;
 mapping the hair from the initial 3D model to the target 3D model;
 interpolating between the initial 3D model and the target 3D model to determine a post-hair growth 3D model of the hair, including:
  generating a complete 3D model of the hair of the person using the person's 3D geometry, texture, shadow, and shading, that includes bone, teeth, gingiva, joint, muscle, soft tissue, and skin information; and
  adding missing data from one or more of the bone, teeth, gingiva, joint, muscle, soft tissue, and skin information from a database of known hair models;
 inputting the coordinates to the post-hair growth 3D model;
 rendering a 2D photo realistic image of the hair of the person based on the post hair growth 3D model; and
 displaying the 2D photo realistic image;
 wherein the method is performed by a computer.

2. The method of claim 1, comprising, extracting environment information from the generated model.

3. The method of claim 1, wherein the generated model is represented using one of: polyhedrons and voxels.

4. The method of claim 1, wherein the generated model is generated after a haircut of the person's hair.

5. The method of claim 1, comprising geometry subdividing and tessellating the generated model.

6. A method for visualizing changes in a three dimensional (3D) model, comprising:
 generating initial environmental information by placing light sources at known coordinates when an initial 2D photograph of a surgical area of a patient is taken;
 receiving the initial 2D photograph of the surgical area before the patient receives plastic surgery;
 receiving an initial 3D model of the surgical area before the patient receives plastic surgery;
 designing a virtual treatment for the surgical area of the patient based at least partially on the initial 2D photograph and the initial 3D model, wherein designing the virtual treatment includes specifying a treatment process in which the patient's surgical area is modified according to a plastic surgery procedure;
 determining a target 3D model of the surgical area of the patient based on the initial 3D model and the virtual treatment;
 mapping the surgical area from the initial 3D model to the target 3D model;
 interpolating between the initial 3D model and the target 3D model to determine a post-treatment 3D model of the surgical area, including:
  generating a complete 3D model of the surgical area of the patient using the person's 3D geometry, texture, shadow, and shading that includes bone, teeth, gingiva, joint, muscle, soft tissue, and skin information; and
  adding missing data from one or more of the bone, teeth, gingiva, joint, muscle, soft tissue, and skin information from a database of known surgical models;
 inputting the coordinates to the post-treatment 3D model;
 rendering a 2D photo realistic image of the surgical area of the patient based on the post-treatment 3D model; and
 displaying the 2D photo realistic image;
 wherein the method is performed by a computer.

7. The method of claim 6, comprising extracting environment information from the generated model.

8. The method of claim 6, wherein the generated model is represented using one of: polyhedrons and voxels.

9. The method of claim 6, comprising geometry subdividing and tessellating the generated model.

10. A method for visualizing changes in a three dimensional (3D) model, comprising:
generating initial environmental information by placing light sources at known coordinates when an initial 2D photograph of a wound of a patient is taken;
receiving the initial 2D photograph of the wound of the patient;
receiving an initial 3D model of the wound of the patient;
modeling a virtual healing of the wound of the patient based at least partially on the initial 2D photograph and the initial 3D model, wherein designing the virtual healing includes specifying a process in which the wound of the patient heals;
determining a target 3D model of the wound of the patient based on the initial 3D model and the virtual treatment;
mapping the wound from the initial 3D model to the target 3D model;
interpolating between the initial 3D model and the target 3D model to determine a post-treatment 3D model of the wound, including:
generating a complete 3D model of the wound of the patient using the person's 3D geometry, texture, shadow and shading that includes bone, teeth, gingiva, joint, muscle, soft tissue and skin information; and
adding missing data from one or more of the bone, teeth, gingiva, joint, muscle, soft tissue, and skin information from a database of known wound models;
inputting the coordinates to the post-treatment 3D model;
rendering a 2D photo realistic image of the wound of the patient based on the post-treatment 3D model; and
displaying the 2D photo realistic image;
wherein the method is performed by a computer.

11. The method of claim 10, comprising extracting environment information from the generated model.

12. The method of claim 10, wherein the wound is on a face of the patient.

13. A method for visualizing changes in a three dimensional (3D) model, comprising:
generating initial environmental information by placing light sources at known coordinates when an initial 2D photograph of a face of a person is taken;
receiving the initial 2D photograph of the face of the person;
receiving an initial 3D model of the face of the person;
designing a virtual treatment for the face of the person based at least partially on the initial 2D photograph and the initial 3D model, wherein designing the virtual treatment includes modifying at least one visual feature of the face of the person;
determining a target 3D model of the face of the person based on the initial 3D model and the virtual treatment;
mapping features from the initial 3D model to the target 3D model;
interpolating between the initial 3D model and the target 3D model to determine an intermediate 3D model, including:
generating a complete 3D model of the face of the person using the person's 3D geometry, texture, shadow, and shading that includes bone, teeth, gingiva, joint, muscle, soft tissue, and skin information; and
adding missing data from one or more of the bone, teeth, gingiva, joint, muscle, soft tissue, and skin information from a database of known facial models;
inputting the coordinates to the intermediate 3D model; and
rendering a 2D photo realistic image based on the intermediate 3D model;
wherein the method is performed by a computer.

14. The method of claim 13 further comprising comparing a scanned face of the person to one or more additional 3D models of the face of the person.

15. The method of claim 13, wherein tile method includes:
texture mapping a picture of the face of the person onto the initial 3D model of the face;
providing surface texture, shadow, and shading information from the picture to the 3D model of the face; and
separating the person's color pigment information from shadow and shading information derived from the picture.

16. The method of claim 13, wherein generating the complete 3D model of the face of the person includes generating a hierarchical model of the bone, teeth, gingiva, joint, muscle, soft tissue, and skin information such that a change in a position or shape of one information level in the hierarchical model changes all dependent information levels in the hierarchical model.

17. A method for visualizing changes in a three dimensional (3D) model, comprising:
generating initial environmental information by placing light sources at known coordinates when an initial 2D photograph of a patient's teeth is taken;
receiving the initial 2D photograph of the patient's teeth prior to treatment;
receiving an initial 3D model of the patient's teeth prior to treatment;
designing a virtual treatment for the patient's teeth based at least partially on the initial 2D photograph and the initial 3D model, wherein designing the virtual treatment includes specifying a treatment process in which the patient's teeth are moved according to an orthodontic treatment;
determining a target 3D model of the patient's teeth based on the initial 3D model and the virtual treatment;
mapping the patient's teeth from the initial 3D model to the target 3D model;
interpolating between the initial 3D model and the target 3D model to determine a post-treatment 3D model of the patient's teeth, including:
generating a complete 3D model of the patient's teeth using the person's 3D geometry, texture, shadow and shading that includes bone, teeth, gingiva, joint, muscle, soft tissue and skin information; and
adding missing data from one or more of the bone, teeth, gingiva, joint, muscle, soft tissue, and skin information from a database of known teeth models;
inputting the coordinates to the post-treatment 3D model;
rendering a 2D photo realistic image of the patient's teeth based on the post-treatment 3D model; and
displaying the 2D photo realistic image;
wherein the method is performed by a computer.

18. The method of claim 17, wherein 3D morphing of the initial 3D model based on the virtual treatment results in a predicted position of the patient's teeth after the orthodontic treatment.

19. The method of claim 18, wherein designing the virtual treatment includes combining texture, environment, shadow, and shading information with the initial 3D model.

20. The method of claim 19, wherein 3D morphing of the initial 3D model includes computing an impact of a movement of one or more of the patient's teeth on at least another of the patient's teeth.

21. The method of claim 19, wherein the initial 3D model and the post-treatment 3D model include a facial model of the patient, and wherein 3D morphing of the initial 3D model includes computing an impact of a movement of one or more of the patient's teeth on the facial model.

22. The method of claim 21, wherein 3D morphing of the initial 3D model includes simulating changes to the facial model due to localized changes in tooth, position using a curves and surfaces based smoothing algorithm.

23. The method of claim 20, wherein the method includes:
mapping feature points to the initial and the post-treatment 3D models; and
interpolating between the initial and tile post-treatment 3D models to determine one or more intermediate 3D models.

24. The method of claim 18, wherein designing the virtual treatment includes specifying each tooth, movement during the orthodontic treatment.

25. The method of claim 24, wherein generating the post-treatment 3D model includes extrapolating missing data on a particular one of the patient's teeth according to information in a database of known tooth shapes.

* * * * *